United States Patent [19]

Konno et al.

[11] Patent Number: 4,659,365

[45] Date of Patent: Apr. 21, 1987

[54] HERBICIDAL 2-CHLORO-2'-FLUOROALKOXYACETANILIDES

[75] Inventors: Kazuhiko Konno; Koichi Araki; Kaoru Ikeda; Keiji Endo; Mitsuru Hikido, all of Ibaraki, Japan

[73] Assignee: Mitsubishi Petrochemical Co., Ltd., Tokyo, Japan

[21] Appl. No.: 769,123

[22] Filed: Aug. 26, 1985

[30] Foreign Application Priority Data

Aug. 29, 1984 [JP] Japan ................. 59-179974

[51] Int. Cl.⁴ ............ A01N 37/24; A01N 43/56; C07C 103/375; C07D 231/12
[52] U.S. Cl. .......................... 71/92; 71/118; 548/375; 548/376; 548/377; 548/378; 564/214
[58] Field of Search ............ 548/375, 376, 377, 378; 564/214; 71/92, 118

[56] References Cited

U.S. PATENT DOCUMENTS 4,593,104  6/1986  Eicken et al. ............ 548/378

FOREIGN PATENT DOCUMENTS 2135301  8/1984  United Kingdom ............ 564/214

*Primary Examiner*—Richard A. Schwartz
*Assistant Examiner*—Kurt G. Briscoe
*Attorney, Agent, or Firm*—Oblon, Fisher, Spivak, McClelland & Maier

[57] ABSTRACT

An acetanilide derivative of the following formula (I) and a herbicide containing one or more of the acetanilide derivative as the active ingredient are described.

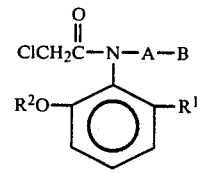

In the formula, $R^1$ is a lower alkyl group; $R^2$ is a fluorine-substituted lower alkyl group; A is

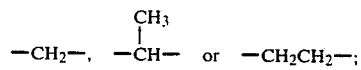

B is an optionally substituted pyrazolyl group, an optionally substituted alkoxy group or a hydrogen atom.

The acetanilide derivative and the herbicide have a selective weed killing activity to gramiveous weeds.

5 Claims, No Drawings

HERBICIDAL 2-CHLORO-2'-FLUOROALKOXYACETANILIDES

BACKGROUND OF THE INVENTION

The present invention relates to novel acetanilide derivatives of the following formula (I):

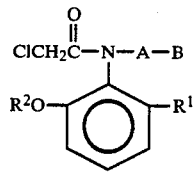

(wherein $R^1$ is a lower alkyl group; $R^2$ is a fluorine-substituted lower alkyl group; A is

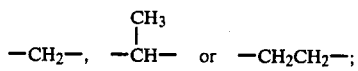

B is an optionally substituted pyrazolyl group, an optionally substituted alkoxy group or a hydrogen atom), as well as a herbicide containing one or more of these acetanilide derivatives as the active ingredient.

Haloacetanilides having herbicidal or growth controlling actions are known. For instance, U.S. Pat. No. 3,547,620 discloses 2-chloro-2',6'-diethyl-N-methoxymethyl acetanilide (hereunder abbreviated as compound A), and Unexamined Published Japanese Patent Application No. 53651/78 discloses 2-chloro-2',6'-dimethyl-N-pyrazolylmethyl acetanilide (hereunder abbreviated as compound B).

Chloroacetanilide compounds of the type shown above generally exhibit herbicidal effects on monocotyledonous plants when applied in soil treatment. For example, compound B as applied to the treatment of soil in upland farm exhibits good herbicidal activities but is very poor in selectivity for crop species. On the other hand, compound A is currently used in actual crop fields on account of its high selectivity for corn (*Zea mays*), soybean (*Glycine max*) and cotton (*Gossypium hirsutum*). However, the herbicidal activity of compound A is relatively low as compared with compound B and needs further enhancement.

SUMMARY OF THE INVENTION

In order to meet the demand just mentioned, the present inventors synthesized a variety of compounds and studied their herbicidal activities and crop selectivity with a view to obtaining chloroacetanilide derivatives having high herbicidal activity and good selectivity for crop species. As a result, the inventors have accomplished the present invention which will be described hereinafter.

The first aspect, therefore, of the present invention is to provide novel acetanilide derivatives of the following formula (I):

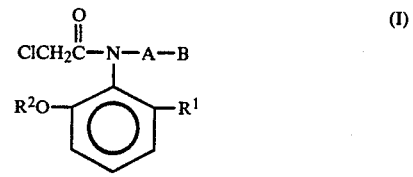

(wherein $R^1$ is a lower alkyl group; $R^2$ is a fluorine-substituted lower alkyl group; A is $$-CH_2-, \quad -\overset{CH_3}{\underset{|}{CH}}- \quad \text{or} \quad -CH_2CH_2-;$$

B is an optionally substituted pyrazolyl group, an optionally substituted alkoxy group or a hydrogen atom).

The second aspect of the invention is to provide a herbicide containing one or more of such novel acetanilide derivatives as the active ingredient.

DETAILED DESCRIPTION OF THE INVENTION

The novel acetanilide derivatives in accordance with the first aspect of the present invention are represented by formula (I):

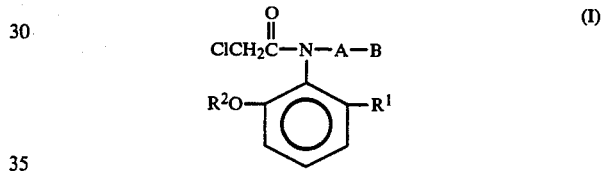

In this formula (I), $R^1$ is a lower alkyl group of $C_1$–$C_4$ such as a methyl group, an ethyl group, a n-propyl group, a iso-propyl group, a n-butyl group or a t-butyl group; $R^2$ is fluorine-substituted lower alkyl group of $C_1$–$C_4$ such as $-CH_2F$, $-CHF_2$, $-CF_3$, $-CH_2CH_2F$, $-CF_2CHF_2$, $-CH_2CF_3$, $-CHFCH_2F$ or $-CF_2CH_2F$; A is $$-CH_2-, \quad -\overset{CH_3}{\underset{|}{CH}}- \quad \text{or} \quad -CH_2CH_2-;$$

B is a pyrazolyl group or lower alkoxy group of $C_1$–$C_4$ that may be substituted by a lower alkyl group of $C_1$–$C_4$, a lower alkoxy group of $C_1$–$C_4$, a halogen atom, a nitro group, a cyano group or a haloalkyl group, or a hydrogen atom.

Specific examples of the novel acetanilide derivatives of formula (I) are listed below:

2-chloro-2'-difluoromethoxy-6'-methyl-N-pyrazolylmethyl acetanilide, 2-chloro-6'-methyl-N-pyrazolylmethyl-2'-(2,2,2-trifluoroethoxy)acetanilide, 2-chloro-2'-(2-fluoroethoxy)-6'-methyl-N-pyrazolylmethyl acetanilide, 2-chloro-6'-methyl-N-pyrazolylmethyl-2'-trifluoromethoxy acetanilide, 2-chloro-6'-methyl-N-pyrazolylmethyl-2'-(1,1,2,2-tetrafluoroethoxy)acetanilide, 2-chloro-2'-fluoromethoxy-6'-methyl-N-pyrazolylmethyl acetanilide, 2-chloro-6'-methyl-2'-pentafluoroethoxy-N-pyrazolylmethyl acetanilide, 2-chloro-2'-difluoromethoxy-6'-ethyl-N-pyrazolylmethyl acetanilide, 2-chloro-6'-ethyl-N-pyrazolylmethyl-2'-(2,2,2-trifluoroethoxy)acetanilide, 2-chloro-6'-ethyl-2'-(2-fluoroethoxy)-N-pyrazolylmethyl acetanilide, 2-chloro-6'-ethyl-N-pyrazolylmethyl-2'-trifluoromethoxy acetanilide, 2-chloro-6'-ethyl-N-pyrazolylmethyl-2'-(1,1,2,2-tetrafluoroethoxy)acetanilide, 2-chloro-2'-difluoromethoxy-6'-isopropyl-N-pyrazolylmethyl acetanilide, 2-chloro-2'-difluoromethoxy-N-(3,5-dimethylpyrazolyl)methyl-6'-methyl acetanilide, 2-chloro-N-(3,5-dimethylpyrazolyl)methyl-6'-methyl-2'-(2,2,2-trifluoroethoxy)acetanilide, 2-chloro-N-(3,5-dimethylpyrazolyl)methyl-2'-(2-fluoroethoxy)-6'-methyl acetanilide, 2-chloro-N-(3,5-dimethylpyrazolyl)methyl-6'-methyl-2'-(2,2,2-trifluoroethoxy)acetanilide, 2-chloro-N-(3,5-dimethylpyrazolyl)methyl-6'-methyl-2'-(1,1,2,2-tetrafluoroethoxy)acetanilide, 2-chloro-2'-difluoromethoxy-N-(3,5-dimethypyrazoyl)methyl-6'-ethyl acetanilide, 2-chloro-2'-difluoromethoxy-6'-methyl-N-(1-pyrazolylethyl-1-yl)acetanilide, 2-chloro-6'-methyl-N-(1-pyrazolylethyl-1-yl)-2'-(2,2,2-trifluoroethoxy)acetanilide, 2-chloro-2'-(2-fluoroethoxy)-6'-methyl-N-(1-pyrazolylethyl-1-yl)acetanilide, 2-chloro-6'-methyl-N-(1-pyrazolylethyl-1-yl)-2'-trifluoromethoxy acetanilide, 2-chloro-6'-methyl-2'-N-(1-pyrazolylethyl-1-yl)-(1,1,2,2-tetrafluoroethoxy)acetanilide, 2-chloro-2'-difluoromethoxy-6'-methyl-N-(1-pyrazolylethyl-1-yl)acetanilide, 2-chloro-6'-ethyl-N-(1-pyrazolylethyl-1-yl)-2'-(2,2,2-trifluoroethoxy)acetanilide, 2-chloro-2'-difluoromethoxy-N-ethoxymethyl-6'-methyl acetanilide, 2-chloro-N-ethoxymethyl-6'-methyl-2'-(2,2,2-trifluoroethoxy)acetanilide, 2-chloro-N-ethoxymethyl-2'-(2-fluoroethoxy)-6'-methyl acetanilide, 2-chloro-N-ethoxymethyl-6'-methyl-2'-trifluoroethoxy acetanilide, 2-chloro-N-ethoxymethyl-6'-methyl-2'-(1,1,2,2-tetrafluoroethoxy)acetanilide, 2-chloro-2'-difluoromethoxy-N-ethoxymethyl-6'-ethyl acetanilide, 2-chloro-2'-difluoromethoxy-N-methoxymethyl-6'-methyl acetanilide, 2-chloro-N-methoxymethyl-6'-methyl-2'-(2,2,2-trifluoroethoxy)acetanilide, 2-chloro-2'-(2-fluoroethoxy)-N-methoxymethyl-6'-methyl acetanilide, 2-chloro-N-methoxymethyl-6'-methyl-2'-trifluoromethoxy acetanilide, 2-chloro-N-methoxymethyl-6'-methyl-2'-(1,1,2,2-tetrafluoroethoxy)acetanilide, 2-chloro-2'-difluoromethoxy-6'-ethyl-N-methoxymethyl-acetanilide, N-n-butoxymethyl-2-chloro-2'-difluoromethoxy-6'-methyl acetanilide, 2-chloro-2'-difluoromethoxy-6'-methyl-N-methyl acetanilide, 2-chloro-2'-difluoromethoxy-N-ethyl-6'-methyl acetanilide, 2-chloro-2'-difluoromethoxy-N-(2-methoxyethyl-1-yl)-6'-methyl acetanilide, 2-chloro-N-(2-ethoxyethyl-1-yl)-2'-difluoromethoxy-6'-methyl acetanilide, 2-chloro-2'-difluoromethoxy-6'-methyl-N-(2-n-propoxyethyl-1-yl)acetanilide, and 2-chloro-2'-difluoromethoxy-6'-ethyl-N-(2-methoxyethyl-1-yl)acetanilide.

The novel acetanilide derivatives of formula (I) may be prepared by one of the following two methods:

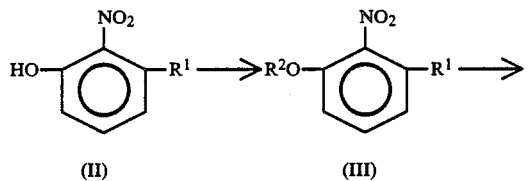

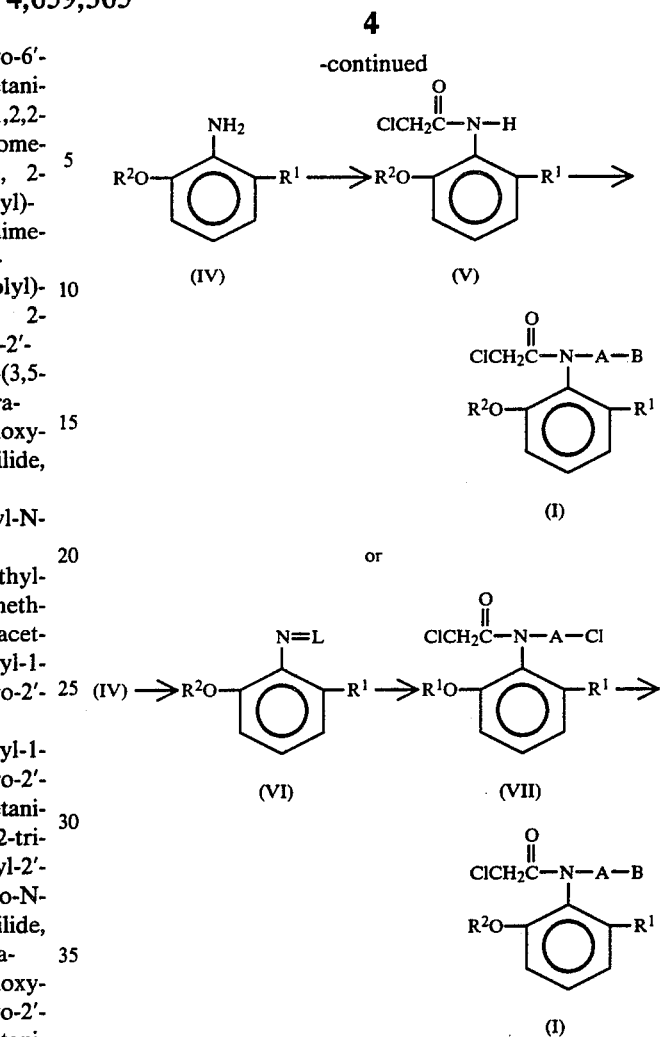

(wherein $R^1$ is a lower alkyl group; $R^2$ is a fluorine-substituted lower alkyl group; A is

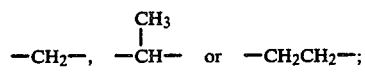

B is an optionally substituted pyrazolyl group, an optionally substituted alkoxy group, or a hydrogen atom; L is $CH_2$ or $CH-CH_3$).

The methods outlined above are hereunder described step by step. First, the synthesis of a 2-fluoroalkoxy-6-alkyl-nitrobenzene derivative of formula (III) from a 3-alkyl-2-nitro-phenol derivative of formula (II) is described.

The compound of formula (II) is reacted with 1 to 2 equivalents of an alkylating agent of $R^2X$ (wherein $R^2$ is the same as defined above; X is chlorine, bromine, iodine or $R^3SO_2-O-$; and $R^3$ is a lower alkyl group, a phenyl group or a p-toluyl group) in an inert solvent in the presence of a base so as to provide the compound of formula (III). The bases that can be used in this reaction include sodium hydroxide, potassium hydroxide, potassium carbonate, sodium carbonate and sodium hydride, etc. Usable reaction solvents include dimethylformamide, dimethylsulfoxide, dioxane, methyl ethyl ketone, water and alcohol, etc. The reaction can be performed at temperatures in the range of 0° C. to the boiling point of the particular solvent used. The reaction period will vary with the reaction temperature and the types of reagents employed. By way of illustration, reaction times ranging from about 1 to 20 hours may be used.

After completion of the reaction, the product may be purified by any of the conventional techniques including column chromatography, distillation, recrystallization, etc.

The 2-alkyl-6-fluoroalkoxy aniline derivatives represented by formula (IV) are prepared by reducing the 2-alkyl-6-fluoroalkoxynitrobenzene derivatives of formula (III).

Any of the methods commonly used in the reduction of a nitro group may be used and they include the following: (1) catalytic reduction using a Raney nickel, Pd on carbon or platinum oxide as a catalyst; (2) reduction in alcohol using zinc powder and a catalytic amount of calcium chloride; and (3) reduction in ethanol using tin chloride or within ethanol containing concentrated hydrochloric acid.

The desired novel acetanilide derivatives of formula (I) may be prepared from the compounds of formula (IV) by, for example, one of the following two routes.

In the first method, the compound of formula (IV) is reacted with 1 to 2 equivalents of chloroacetyl chloride in an inert solvent in the presence of 1 to 2 equivalents of a base as an agent to remove hydrogen halide, thereby producing a 2′-alkyl-2-chloro-6′-fluoroalkoxy acetanilide derivative of formula (V).

This reaction is performed in an inert solvent such as an aromatic hydrocarbon (e.g., toluene or benzene), an ether (e.g., tetrahydrofuran, diethyl ether or dioxane), a hydrocarbon halide (e.g., chloroform or dichloromethane), ethyl acetate, acetone or acetonitrile.

Bases that can be used as agents to remove hydrogen halide include sodium hydroxide, potassium hydroxide, potassium carbonate, sodium carbonate, pyridine and triethylamine. There is no particular limitation on the temperature that can be used in the reaction and by way of example, it may be performed in the range of temperatures from those obtained by ice cooling up to the boiling point of the particular solvent used. The reaction times will vary with the reaction temperature and the type of the particular agent used to remove hydrogen halide. As a guide figure, reaction times in the range of about 1 to 20 hours may be used. After completion of the reaction, the product may be purified by conventional techniques including column chromatography or recrystallization.

In the next step, the compound of formula (V) is reacted with 1 to 2 equivalents of an alkylating agent of the formula A—B—X (wherein A, B and X are the same as defined above) or a hydrochloric acid salt thereof in an inert organic solvent or a two-component system made of water and an organic solvent, in the presence of both 1 to 50 wt%, preferably 5 to 30 wt%, of a phase-transfer catalyst and 1 to 5 equivalents of a base, thereby producing the novel acetanilide derivative of formula (I).

Illustrative inert organic solvents that can be used in this reaction include dichloromethane, tetrahydrofuran, dimethylformamide and dimethylsulfoxide, etc. Exemplary bases are sodium hydroxide, potassium hydroxide and sodium hydride, etc. Examples of phase-transfer catalysts that can be used in the reaction include quaternary ammonium salts such as tetramethyl ammonium chloride, tetrabutyl ammonium bromide and benzyl tributyl ammonium chloride, and quaternary phosphonium salts such as tetraphenyl phosphonium bromide.

The reaction may be carried out at any temperature in the range of about 0° to 100° C. The reaction period will vary with the reaction temperature and the type of the catalyst used, and by way of example, reaction times in the range of about 1 to 20 hours may be employed. After completion of the reaction, the product may be purified by any conventional techniques including column chromatography or recrystallization.

In accordance with the other route by which the novel acetanilide derivative of formula (I) is obtained from the compound of formula (IV), the 2-alkyl-6-fluoroalkoxy aniline derivative of formula (IV) is dehydratively condensed with formalin or anhydrous acetaldehyde to make a 2-alkyl-N,N-alkylidene-6-fluoroalkoxy aniline derivative of formula (VI).

If the dehydrative condensation reaction is performed within a solvent, a suitable aromatic hydrocarbon such as toluene or benzene may be employed as the solvent.

If formalin is used as the reactant with the compound of formula (IV), it is used in an excess amount. The reaction is carried out at a temperature in the range of 50° C. up to the boiling point of the particular solvent for a period of 1 to 3 hours, and the organic layer is heated to effect dehydration by azeotropic distillation. If anhydrous acetaldehyde is used as the reactant with the compound of formula (IV), magnesium sulfate or molecular sieves are used as a dehydrating agent, and after performing reaction at between −20° C. and 30° C. for a period of 2 to 24 hours, the dehydrating agent is filtered off.

After completion of the reaction, the product is simply converted to a crude form by concentrating the solvent. Alternatively, the product may be further purified by distillation, or the reaction solution may be directly subjected to the next stage of reaction.

The 2′-alkyl-N,N-alkylidene-6′-fluoroalkoxy aniline derivative of formula (VI) obtained in the above reaction is then reacted with 1 to 1.5 equivalents of chloroacetyl chloride in a solvent such as an aromatic hydrocarbon (e.g., toluene or benzene) at between −10° C. and 30° C. for a period of about 1 to 3 hours, thereby producing a 2′-alkyl-2-chloro-N-(chloromethyl or 1-chloroethyl-1-yl)-6′-fluoroalkoxy acetanilide derivative of formula (VII).

After completion of the reaction, the solution may be immediately subjected to the next reaction stage. Alternatively, it is simply concentrated in vacuum for use as a crude starting material in the next reaction step.

The reaction solution containing the compound of formula (VII) is reacted with not less than 1.5 equivalents of a pyrazole derivative or a lower alcohol in an inert solvent in the presence of a base, thereby producing the desired novel acetanilide of formula (I).

Illustrative inert solvents that can be used in this last step include toluene, benzene, acetonitrile, tetrahydrofuran, dimethylformamide and mixtures thereof. Exemplary bases that may be used include potassium carbonate, sodium carbonate, sodium hydroxide, potassium hydroxide, triethylamine and pyridine, etc. After completion of the reaction, the product may be purified by any conventional techniques including column chromatography or recrystallization.

Advantages of the Invention

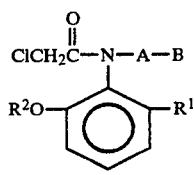

(wherein R$^1$ is a lower alkyl group; R$^2$ is a fluorine-substituted lower alkyl group; A is

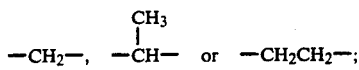

B is an optionally substituted pyrazolyl group, an optionally substituted alkoxy group or a hydrogen atom) in accordance with the present invention are novel undocumented compounds.

These compounds exhibit particularly strong herbicidal effects against a broad species of monocotyledonous weeds, such as barnyardgrass (*Echinochloa crusgalli*), crabgrass (*Digitaria adscendens*), green foxtail (*Setaria viridis*), waterfoxtail (*Alopecurus geniculatus*), *Paspalum thunbergii*, wild oat (*Avena fatua*), annual bluegrass (*Poa annua*) and galingale (*Cyperus microiria*), all of which present problems in the soil and foliage treatments of upland farm. Furthermore, several of the compounds of the present invention will cause no serious damage to principal crops such as corn (*Zea mays*), soybean (*Glycine max*), cotton (*Gossypium hirsutum*), sunflower (*Helianthus annuus*), sugar beet (*Beta vulgaris*) and lawn grass (*Zoisia japonica*). Others exhibit strong herbicidal effects against weeds in poddy lands such as barnyardgrass (*Echinochloa crusgalli*), barnyardgrass (*Echinochloa oryzicola*), waterfoxtail (*Alopecurus geniculatus*), bulrush (*Scirpus juncoides*), japanese ribbon wapato (*Sagittaria pygmaea*), slender spikerush (*Eleocharis accularis*) and water nutgrass (*Cyperus serotinus*), without causing any serious damage to rice (*Oryza sativa*).

It will therefore be understood that the compounds of the present invention and compositions containing one or more of these compounds as the active ingredient can effectively be used as herbicides in paddy lands, upland farms, orchards, pasture land, lawns, forest lands or any other non-agricultural lands.

EXPERIMENTS

The methods for preparing several of the novel acetanilide derivatives in accordance with the present invention are shown below. In the following, identification of the products was made by IR spectroscopy, $^1$H NMR spectroscopy, mass spectroscopy or gas chromatography.

Example 1

Synthesis of 2-nitro-3-(2,2,2-trifluoroethoxy)toluene

To 50 ml of dimethylformamide containing 7.65 g (50 mmol) of 3-methyl-2-nitrophenol, 13.6 g (100 mmol) of potassium carbonate and 12.6 g (60 mmol) of 1-iodo-2,2,2-trifluoroethane were added, and the mixture was heated at 120° to 130° C. under agitation for 2 hours. Water and ether were added to the reaction mixture, and thereafter, the ether layer was concentrated to obtain 11.2 g of 2-nitro-3-(2,2,2-trifluoroethoxy)toluene as an oil.

Example 2

Synthesis of 6-methyl-2-(2,2,2-trifluoroethoxy)aniline

To 60 ml of an ethanol solution containing 10 g (42.6 mmol) of 2-nitro-3-(2,2,2-trifluoroethoxy)toluene, 1 g of 5 wt% Pd-carbon catalyst, and catalytic reduction was performed at atmospheric pressure and room temperature. After performing thin-layer chromatography to confirm that all the starting material had been consumed, the catalyst was filtered off and the filtrate was concentrated to provide 8.7 g of 2-methyl-6-(2,2,2-trifluoroethoxy)aniline as an oil.

Example 3

Synthesis of 2-chloro-2'-methyl-6'-(2,2,2-trifluoroethoxy)acetanilide

To 50 ml of an acetone solution containing 8.0 g (39 mmol) of 2-methyl-6-(2,2,2-trifluoroethoxy)aniline, 8.0 g (58 mmol) of potassium carbonate was added. Thereafter, 5.3 g (47 mmol) of chloroacetyl chloride was added dropwise under ice cooling, and the mixture was stirred for 1 hour.

To the reaction mixture thus obtained, 150 ml of water was added and the precipitating crystal was recovered by filtration, washed with water and dried to provide 10.7 g of 2-chloro-2'-methyl-6'-(2,2,2-trifluoroethoxy)acetanilide, having a melting point of 128° to 129° C.

Example 4

Synthesis of 2-chloro-2'-methyl-N-pyrazolylmethyl-6'-(2,2,2-trifluoroethoxy)acetanilide To 14.2 g (178 mmol) of a 50% aqueous solution of sodium hydroxide, 60 ml of a dichloromethane solution containing 10 g (35.5 mol) of 2-chloro-2'-methyl-6'-(2,2,2-trifluoroethoxy)acetanilide was added under ice cooling. To the ice-cooled reaction mixture, 0.5 g of benzyl tributyl ammonium chloride was added, followed by addition of 10.9 g (71 mmol) of 1-chloromethyl pyrazole hydrochloric acid salt. Under cooling with ice, the mixture was agitated for 30 minutes, and then, it was further stirred at room temperature for 1 hour. To the reaction mixture, 100 ml of dichloromethane was added. The organic layer was separated and washed with water two or three times. Thereafter, the layer was dried over anhydrous magnesium sulfate and passed through a filter. The filtrate was concentrated in vacuum and the resulting oily product was subjected to column chromatography on silica gel. By elution from n-hexane/ethyl acetate (4:1) mixture, 10.3 g of 2-chloro-2'-methyl-N-pyrazolylmethyl-6'-(2,2,2-trifluoroethoxy)acetanilide (Compound No. 2) was obtained. This compound had a melting point of 104° to 105° C.

Mass spectrum: m/e 361

IR (KBr tab.): 1685 cm$^{-1}$ $^1$H NMR (CDCl$_3$) δ: 1.82 (3H, S); 3.70 (2H, S); 4.20 (2H, t, J=8.0 Hz); 5.80 (2H, ABq); 6.23 (H, m); 6.63–7.47 (3H, m); 7.23 (H, m); 7.80 (H, m).

Example 5

Synthesis of 3-difluoromethoxy-2-nitro toluene

To 125 ml of a dioxane solution containing 12.7 g (83 mmol) of 3-methyl-2-nitro phenol, 150 ml of an aqueous solution containing 26.5 g (660 mmol) of sodium hydroxide was added, and the mixture was vigorously agitated while heating to 60° C. Chlorodifluoromethane gas was bubbled into the reaction mixture until no 3-methyl-2-nitrophenol was found to be present by thin-layer chromatography. After completion of the reaction, the reaction mixture was cooled to room temperature and extracted with ether. The extract was washed with water until it became neutral. The extract was then dried over anhydrous magnesium sulfate and the solvent was distilled off to obtain 16.8 g of 3-difluoromethoxy-2-nitrotoluene as an oil.

Example 6

Synthesis of 2-difluoromethoxy-6-methyl aniline

The procedures of Example 2 were repeated except that the starting material was 16.0 g (79 mmol) of 3-difluoromethoxy-2-nitrotoluene as dissolved in 100 ml of ethanol. As a result, 13.0 g of 2-difluoromethoxy-6-methyl aniline was obtained.

Example 7

Synthesis of 2-chloro-2'-difluoromethoxy-6'-methyl acetanilide

The procedures of Example 3 were repeated except that the starting material was 50 ml of an acetone solution containing 8.9 g (51 mmol) of 2-difluoromethoxy-6-methyl aniline, to which 10.5 g (77 mmol) of potassium carbonate and 7.0 g (62 mmol) of chloroacetyl chloride were added. As a result, 12.0 g of 2-chloro-2'-difluoromethoxy-6'-methylacetanilide was obtained. It had a melting point of 85° to 86° C.

Example 8

Synthesis of 2-chloro-2'-difluoromethoxy-6'-methyl-N-pyrazolyl-methyl acetanilide To 14.1 g (176.3 mmol) of a 50% sodium hydroxide solution, 70 ml of a dichloromethane solution containing 8.8 g (35 mmol) of 2-chloro-2'-difluoromethoxy-6'-methyl acetanilide was added under ice cooling. To the ice-cooled mixture, 0.5 g of benzyl tributyl ammonium chloride and 10.8 g (71 mmol) of 1-chloromethyl-pyrazole hydrochloric acid salt were added. The mixture was subsequently treated in the same manner as in Example 4 to produce 9.3 g of 2-chloro-2'-difluoromethoxy-6'-methyl-N-pyrazolylmethyl acetanilide (Compound No. 1). It had a melting point of 121° to 122.5° C.

Mass spectrum: m/e 329

IR (KBr tab.): 1700 cm$^{-1}$ $^1$H NMR (CDCl$_3$) δ: 3.76 (2H, S); 3.92 (3H, S); 5.85 (2H, ABq); 6.20 (H, m); 6.50 (H, t, J=72.0 Hz); 6.93–7.33 (3H, broad); 7.35 (H, d); 7.82 (H, d).

The compounds prepared above, as well as those prepared in a similar manner in accordance with the present invention, are identified below in terms of formula (I)

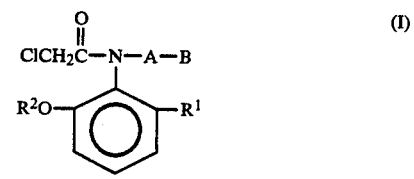

In the designations used below, Me stands for a methyl group.

| Compound No. | R$_1$ | R$_2$ | A | B | Appearance or Physical Properties |
|---|---|---|---|---|---|
| 1 | Me | —CF$_2$H | —CH$_2$— | -N-N (pyrazolyl) | m.p. 121–122.5° C. |
| 2 | Me | —CH$_2$CF$_3$ | —CH$_2$— | -N-N (pyrazolyl) | m.p. 104–105° C. |
| 3 | Me | —CH$_2$CH$_2$F | —CH$_2$— | -N-N (pyrazolyl) | m.p. 90–92° C. |
| 4 | Me | —CF$_2$H | —CH$_2$— | -N-N (dimethylpyrazolyl) | m.p. 104–105° C. |
| 5 | Me | —CH$_2$CF$_3$ | —CH$_2$— | -N-N (dimethylpyrazolyl) | m.p. 126–127° C. |

-continued

| Compound No. | R₁ | R₂ | A | B | Appearance or Physical Properties |
|---|---|---|---|---|---|
| 6 | Me | $-CH_2CH_2F$ | $-CH_2-$ | $-N\underset{Me}{\overset{N}{\diagdown}}-Me$ (dimethylpyrazole) | m.p. 125–127° C. |
| 7 | Me | $-CF_2H$ | $-CH(CH_3)-$ | $-N\diagdown N$ (pyrazole) | m.p. 82.5–83.5° C. |
| 8 | Me | $-CH_2CF_3$ | $-CH(CH_3)-$ | $-N\diagdown N$ (pyrazole) | m.p. 75–77° C. |
| 9 | Me | $-CH_2CH_2F$ | $-CH(CH_3)-$ | $-N\diagdown N$ (pyrazole) | wax |
| 10 | Me | $-CF_2H$ | $-CH_2-$ | $-OC_2H_5$ | $n_D^{25}$ 1.4994 |
| 11 | Me | $-CH_2CF_3$ | $-CH_2-$ | $-OC_2H_5$ | m.p. 62–62.5° C. |
| 12 | Me | $-CH_2CH_2F$ | $-CH_2-$ | $-OC_2H_5$ | $n_D^{25}$ 1.5075 |
| 13 | Me | $-CF_2H$ | $-CH_2-$ | $-OCH_3$ | $n_D^{25}$ 1.5040 |
| 14 | Me | $-CH_2CF_3$ | $-CH_2-$ | $-OCH_3$ | $n_D^{25}$ 1.4911 |
| 15 | Me | $-CH_2CH_2F$ | $-CH_2-$ | $-OCH_3$ | $n_D^{25}$ 1.5233 |
| 16 | Me | $-CHF_2$ | $-CH_2CH_2-$ | $-OCH_3$ | $n_D^{25}$ 1.5032 |
| 17 | Me | $-CHF_2$ | $-CH_2-$ | $-H$ | $n_D^{25}$ 1.5082 |
| 18 | Et | $-CHF_2$ | $-CH_2-$ | $-OCH_3$ | $n_D^{20}$ 1.4990 |
| 19 | Et | $-CHF_2$ | $-CH_2-$ | $-OC_2H_5$ | $n_D^{20}$ 1.4994 |
| 20 | Et | $-CHF_2$ | $-CH_2-$ | $-N\diagdown N$ (pyrazole) | m.p. 92–93° C. |
| 21 | Et | $-CHF_2$ | $-CH_2CH_2-$ | $-OCH_3$ | $n_D^{20}$ 1.5042 |

As will be shown later in the Tests, the novel acetanilide derivatives of the present invention exhibit strong actions when used as the active ingredient of a herbicide. It is particularly noteworthy that the derivatives have selective herbicidal activities in that they kill gramineous weeds without causing any damage to crops such as corn (*Zea mays*), soybean (*Glycine max*), cotton (*Gossypium hirsutum*), sugar beet (*Beta vulgaris*) and sunflower (*Helianthus annuus*).

The derivatives and herbicides containing them as the active ingredient have a wide scope of applications not only in upland farms but also in paddy lands, orchards, mulberry fields, forest lands and even in non-agricultural lands.

In actual applications, the derivatives and herbicides containing them as the active ingredient may be dispersed in water or formulated in various forms such as emulsifiable concentrates, liquid formulations, wettable powders, dusts and granules by incorporating a variety of adjuvants such as diluents, solvents, emulsifiers and spreaders.

It is difficult to give the precise level of an appropriate dose of the herbicide containing the novel compounds of the present invention since this will greatly vary with the weather, soil, drug formulation, seasonal timing of application, its method and the target weed. However, it can generally be stated that satisfactory results will be ensured by applying 0.015 to 10 kg of the herbicide per hectare, and the preferred range is 0.25 to 5 kg/hectare.

The herbicide containing the novel compounds of the present invention as the active ingredient may be used in combination with other agrichemicals such as herbicides, insecticides and fungicides. Alternatively, the herbicide may be mixed with fertilizers or soil. Even better results may be obtained by combining the herbicide with other agrichemicals or mixing it with fertilizers or soil.

The advantages of the herbicide in accordance with the present invention are hereunder described by reference to plant tests and formulation examples. It should however be understood that the scope of the present invention is by no means limited to the following description.

Test 1: Pre-emergence treatment under flooded conditions

Plastic pots having an area of 200 cm² were filled with paddy land soil containing fertilizers. After addition of water, the respective components were intimately mixed and the seeds (of test weeds) were sown. Four rice seedlings that had grown to the 2.5-leaf stage were transplanted into each of the pots.

Three days after the transplantation and sowing, selected samples of the compounds of the present invention that had been formulated as wettable powders (see Preparation 2 below) were applied at desired dosage. Thirty days after this treatment, the herbicidal effects of the compounds and the degree of damage to rice (*Oryza sativa*) were evaluated (or rated), and the results are shown in Table I, wherein each of the two parameters is evaluated on a 6-score basis, the herbicidal effects being indicated by numerals and the damage to rice being expressed by symbols.

| Rating | Herbicidal activity (%) |
|---|---|
| 5 | >95 |
| 4 | 81-94 |
| 3 | 61-80 |
| 2 | 41-60 |
| 1 | 21-40 |
| 0 | 0-20 |

| Crop injury | |
|---|---|
| X, | dead |
| +++, | extensive damage |
| ++, | moderate damage |
| +, | small damage |
| ±, | slight damage |
| -, | no damage |

TABLE I

| Compound No. | Dose (a.i.kg/ha) | Herbicidal Effect | | | | Crop injury |
|---|---|---|---|---|---|---|
| | | Barnyardgrass (Echinochloa crusgalli) | Bulrush (Scirpus juncoides) | Monochoria (Monochoria vaginalis) | Kikashigusa (Rotala indica) | |
| 1 | 1 | 5 | 5 | 5 | 5 | ± |
|  | 0.3 | 5 | 5 | 5 | 5 | ± |
|  | 0.1 | 5 | 5 | 5 | 5 | - |
|  | 0.03 | 5 | 5 | 4 | 4 | - |
| 2 | 1 | 5 | 5 | 5 | 5 | ± |
|  | 0.3 | 5 | 5 | 5 | 5 | ± |
|  | 0.1 | 5 | 5 | 5 | 5 | - |
|  | 0.03 | 5 | 5 | 3 | 4 | - |
| 3 | 1 | 5 | 5 | 5 | 5 | - |
|  | 0.3 | 5 | 5 | 5 | 5 | - |
|  | 0.1 | 5 | 4 | 4 | 3 | - |
|  | 0.03 | 4 | 3 | 3 | 2 | - |
| 4 | 1 | 5 | 5 | 5 | 5 | ± |
|  | 0.3 | 5 | 5 | 5 | 5 | ± |
|  | 0.1 | 5 | 5 | 5 | 5 | - |
|  | 0.03 | 5 | 5 | 5 | 5 | - |
| 5 | 1 | 5 | 5 | 5 | 5 | ± |
|  | 0.3 | 5 | 5 | 5 | 5 | - |
|  | 0.1 | 5 | 4 | 5 | 4 | - |
|  | 0.03 | 5 | 2 | 5 | 3 | - |
| 6 | 1 | 5 | 5 | 5 | 5 | ± |
|  | 0.3 | 5 | 5 | 5 | 5 | ± |
|  | 0.1 | 5 | 4 | 5 | 5 | - |
|  | 0.03 | 5 | 2 | 2 | 3 | - |
| 7 | 1 | 5 | 5 | 5 | 5 | ± |
|  | 0.3 | 5 | 5 | 5 | 5 | ± |
|  | 0.1 | 5 | 5 | 5 | 5 | - |
|  | 0.03 | 5 | 5 | 4 | 4 | - |
| 8 | 1 | 5 | 5 | 5 | 5 | ± |
|  | 0.3 | 5 | 5 | 5 | 5 | ± |
|  | 0.1 | 5 | 4 | 5 | 5 | - |
|  | 0.03 | 5 | 4 | 4.5 | 4 | - |
| 9 | 1 | 5 | 5 | 5 | 5 | + |
|  | 0.3 | 5 | 5 | 5 | 5 | ± |
|  | 0.1 | 5 | 4.5 | 5 | 4 | ± |
|  | 0.03 | 5 | 4 | 4 | 3 | - |
| 10 | 1 | 5 | 5 | 5 | 5 | ± |
|  | 0.3 | 5 | 5 | 5 | 5 | ± |
|  | 0.1 | 5 | 5 | 3 | 5 | - |
|  | 0.03 | 5 | 3 | 3 | 3 | - |
| 11 | 1 | 5 | 5 | 5 | 5 | ± |
|  | 0.3 | 5 | 5 | 5 | 5 | ± |
|  | 0.1 | 5 | 5 | 5 | 5 | - |
|  | 0.03 | 5 | 5 | 5 | 4 | - |
| 12 | 1 | 5 | 5 | 5 | 5 | + |
|  | 0.3 | 5 | 5 | 5 | 5 | ± |
|  | 0.1 | 5 | 5 | 5 | 5 | ± |
|  | 0.03 | 5 | 5 | 5 | 5 | - |
| 13 | 1 | 5 | 5 | 5 | 5 | ± |
|  | 0.3 | 5 | 5 | 5 | 5 | ± |
|  | 0.1 | 5 | 5 | 4 | 4 | - |
|  | 0.03 | 5 | 4 | 3 | 3 | - |
| 14 | 1 | 5 | 5 | 5 | 5 | ± |
|  | 0.3 | 5 | 5 | 5 | 4 | ± |
|  | 0.1 | 5 | 5 | 5 | 3 | ± |
|  | 0.03 | 5 | 5 | 4 | 3 | - |
| 15 | 1 | 5 | 5 | 5 | 5 | + |
|  | 0.3 | 5 | 5 | 5 | 5 | ± |
|  | 0.1 | 5 | 4 | 3 | 4 | - |
|  | 0.03 | 4.5 | 3 | 3 | 3 | - |
| 16 | 1 | 5 | 5 | 5 | 5 | + |
|  | 0.3 | 5 | 5 | 5 | 5 | ± |
|  | 0.1 | 5 | 5 | 5 | 5 | - |
|  | 0.03 | 5 | 4 | 4 | 5 | - |
| 17 | 1 | 5 | 5 | 5 | 5 | - |
|  | 0.3 | 5 | 5 | 5 | 5 | - |

TABLE I-continued

|  |  | Herbicidal Effect | | | | |
|---|---|---|---|---|---|---|
| Compound No. | Dose (a.i.kg/ha) | Barnyardgrass (Echinochloa crusgalli) | Bulrush (Scirpus juncoides) | Monochoria (Monochoria vaginalis) | Kikashigusa (Rotala indica) | Crop injury |
|  | 0.1 | 4.5 | 4 | 4 | 4 | — |
|  | 0.03 | 4 | 4 | 4 | 3 | — |
| 18 | 1 | 5 | 5 | 5 | 4.5 | + |
|  | 0.3 | 5 | 5 | 5 | 4 | ± |
|  | 0.1 | 5 | 5 | 5 | 2 | — |
|  | 0.03 | 5 | 4.5 | 4.5 | 1 | — |
| 19 | 1 | 5 | 5 | 5 | 4.5 | + |
|  | 0.3 | 5 | 5 | 5 | 4.5 | ± |
|  | 0.1 | 5 | 5 | 5 | 4 | ± |
|  | 0.03 | 5 | 5 | 5 | 3 | — |
| 20 | 1 | 5 | 5 | 5 | 4.5 | + |
|  | 0.3 | 5 | 5 | 5 | 4.5 | ± |
|  | 0.1 | 5 | 5 | 5 | 4.5 | — |
|  | 0.03 | 5 | 5 | 5 | 3 | — |
| 21 | 1 | 5 | 5 | 5 | 5 | + |
|  | 0.3 | 5 | 5 | 5 | 4.5 | ± |
|  | 0.1 | 5 | 5 | 5 | 4.5 | — |
|  | 0.03 | 5 | 5 | 5 | 4 | — |
| Comparative Agent a | 1 | 5 | 5 | 5 | 5 | ± |
|  | 0.3 | 5 | 5 | 5 | 5 | — |
|  | 0.1 | 5 | 5 | 4 | 4 | — |
|  | 0.03 | 5 | 5 | 3 | 3 | — |

Note:
a: 2-chloro-2', 6'-diethyl-N—butoxymethyl acetanilide

Test 2: Treatment in grown stage under flooded condition

Tests were conducted as in Test 1 except that the herbicidal treatment was performed 10 days after sowing and transplantation (Barnyardgrass (Echinochloa crusgalli) in 1.5-leaf stage). The results are shown in Table II.

TABLE II

|  |  | Herbicidal Effect | | | | |
|---|---|---|---|---|---|---|
| Compound No. | Dose (a.i.kg/ha) | Barnyardgrass (Echinochloa crusgalli) | Bulrush (Scirpus juncoides) | Monochoria (Monochoria vaginalis) | Kikashigusa (Rotala indica) | Crop injury |
| 1 | 1 | 5 | 5 | 5 | 5 | ± |
|  | 0.3 | 5 | 5 | 5 | 5 | ± |
|  | 0.1 | 5 | 4 | 4 | 4 | — |
| 2 | 1 | 5 | 5 | 5 | 5 | ± |
|  | 0.3 | 5 | 5 | 5 | 5 | — |
|  | 0.1 | 5 | 5 | 3 | 3 | — |
| 3 | 1 | 5 | 5 | 5 | 4 | ± |
|  | 0.3 | 5 | 3 | 5 | 3 | — |
|  | 0.1 | 5 | 2 | 3 | 2 | — |
| 4 | 1 | 5 | 4 | 5 | 4 | — |
|  | 0.3 | 5 | 3 | 5 | 3 | — |
|  | 0.1 | 4 | 2 | 4 | 2 | — |
| 5 | 1 | 5 | 2 | 5 | 3 | — |
|  | 0.3 | 5 | 1 | 4 | 2 | — |
|  | 0.1 | 4 | 0 | 3 | 0 | — |
| 6 | 1 | 5 | 2 | 5 | 4 | ± |
|  | 0.3 | 5 | 1 | 4 | 3 | — |
|  | 0.1 | 4 | 0 | 3 | 2 | — |
| 7 | 1 | 5 | 5 | 5 | 5 | ± |
|  | 0.3 | 5 | 4 | 5 | 5 | — |
|  | 0.1 | 5 | 3 | 3 | 3 | — |
| 8 | 1 | 5 | 5 | 5 | 5 | ± |
|  | 0.3 | 5 | 4 | 5 | 5 | — |
|  | 0.1 | 5 | 3 | 3 | 3 | — |
| 9 | 1 | 5 | 5 | 5 | 4 | — |
|  | 0.3 | 5 | 3 | 4 | 2 | — |
|  | 0.1 | 4 | 2 | 3 | 1 | — |
| 10 | 1 | 5 | 4 | 5 | 5 | — |
|  | 0.3 | 5 | 3 | 5 | 5 | — |
|  | 0.1 | 4 | 1 | 3 | 2 | — |
| 11 | 1 | 5 | 3 | 5 | 4 | — |
|  | 0.3 | 5 | 2 | 5 | 3 | — |
|  | 0.1 | 5 | 1 | 4 | 2 | — |
| 12 | 1 | 5 | 4 | 5 | 5 | — |
|  | 0.3 | 5 | 3 | 5 | 5 | — |
|  | 0.1 | 5 | 2 | 4 | 4 | — |
| 13 | 1 | 5 | 4 | 5 | 4 | + |
|  | 0.3 | 5 | 3 | 3 | 3 | ± |
|  | 0.1 | 3 | 2 | 2 | 1 | — |
| 14 | 1 | 5 | 4 | 5 | 4 | ± |
|  | 0.3 | 5 | 3 | 3 | 3 | — |

TABLE II-continued

| Compound No. | Dose (a.i.kg/ha) | Herbicidal Effect | | | | Crop injury |
|---|---|---|---|---|---|---|
| | | Barnyardgrass (Echinochloa crusgalli) | Bulrush (Scirpus juncoides) | Monochoria (Monochoria vaginalis) | Kikashigusa (Rotala indica) | |
| 15 | 0.1 | 2 | 2 | 1 | 2 | — |
| | 1 | 5 | 4 | 5 | 4 | ± |
| | 0.3 | 4 | 3 | 4 | 3 | — |
| 16 | 0.1 | 2 | 1 | 1 | 2 | — |
| | 1 | 5 | 5 | 5 | 5 | + |
| | 0.3 | 5 | 5 | 5 | 5 | ± |
| 17 | 0.1 | 4 | 4 | 4 | 3 | — |
| | 1 | 5 | 5 | 5 | 5 | — |
| | 0.3 | 4 | 4 | 4 | 3 | — |
| 18 | 0.1 | 3 | 2 | 2 | 2 | — |
| | 1 | 5 | 3.5 | 5 | 4.5 | ± |
| | 0.3 | 5 | 3 | 4.5 | 4 | — |
| 19 | 0.1 | 4 | 3 | 4.5 | 2 | — |
| | 1 | 5 | 4 | 5 | 5 | ± |
| | 0.3 | 4.5 | 2 | 5 | 3.5 | — |
| 20 | 0.1 | 4.5 | 1 | 4 | 2 | — |
| | 1 | 4.5 | 4 | 5 | 5 | ± |
| | 0.3 | 4.5 | 4 | 5 | 4 | — |
| 21 | 0.1 | 4.5 | 3 | 4.5 | 3 | — |
| | 1 | 5 | 4 | 5 | 5 | ± |
| | 0.3 | 5 | 4 | 5 | 4 | — |
| Comparative Agent a | 0.1 | 4.5 | 2 | 3 | 3 | — |
| | 1 | 5 | 2 | 5 | 4 | — |
| | 0.3 | 4 | 1 | 3 | 2 | — |
| | 0.1 | 2 | 0 | 2 | 0 | — |

Test 3: Pre-emergence treatment under upland condition

Polyethylene vats having an area of 1,000 cm² were filled with sieved upland soil. The test weeds and crop species were sown and covered with a soil layer 1 cm thick. Thereafter, the selected samples of the compound of the present invention formulated as a wettable powder dissolved in 10 ml were sprayed at the desired dosage on the surface of the soil.

Twenty days after the treatment, the herbicidal effects and crop injury were evaluated, and the results are shown in Table III. The rating indices were the same as used in Tests 1 and 2.

TABLE III

| Compound No. | Dose (a.i.kg/ha) | Crop Injury | | | | | Herbicidal Effect | | | | | |
|---|---|---|---|---|---|---|---|---|---|---|---|---|
| | | A | B | C | D | E | F | G | H | I | J | K |
| 1 | 2 | — | — | ± | ± | ++ | 5 | 5 | 5 | 5 | 5 | 5 |
| | 0.5 | — | — | — | — | — | 5 | 5 | 5 | 5 | 5 | 5 |
| | 0.25 | — | — | — | — | — | 5 | 5 | 5 | 5 | 5 | 5 |
| | 0.12 | — | — | — | — | — | 5 | 5 | 5 | 5 | 4 | 3 |
| | 0.06 | — | — | — | — | — | 5 | 5 | 5 | 5 | 3 | 3 |
| 2 | 2 | x | — | — | ++ | x | 5 | 5 | 5 | 5 | 5 | 5 |
| | 0.5 | ± | — | — | — | — | 5 | 5 | 5 | 5 | 5 | 5 |
| | 0.25 | — | — | — | — | — | 5 | 5 | 5 | 5 | 4 | 4 |
| | 0.12 | — | — | — | — | — | 5 | 5 | 5 | 5 | 3 | 3 |
| | 0.06 | — | — | — | — | — | 3.5 | 4 | 4 | 4 | 2 | 0 |
| 3 | 2 | +++ | — | — | — | ± | 5 | 5 | 5 | 5 | 5 | 5 |
| | 0.5 | — | — | — | — | — | 5 | 5 | 5 | 5 | 5 | 5 |
| | 0.25 | — | — | — | — | — | 5 | 5 | 4.5 | 5 | 2 | 2 |
| | 0.12 | — | — | — | — | — | 4 | 4.5 | 1 | 4 | 0 | 0 |
| | 0.06 | — | — | — | — | — | 3 | 4 | 0 | 3 | 0 | 0 |
| 4 | 2 | x | — | — | — | — | 5 | 5 | 5 | 5 | 5 | 4 |
| | 0.5 | ± | — | — | — | — | 5 | 5 | 5 | 5 | 3 | 2 |
| | 0.25 | — | — | — | — | — | 5 | 5 | 5 | 5 | 2 | 1 |
| | 0.12 | — | — | — | — | — | 5 | 5 | 5 | 5 | 0 | 0 |
| | 0.06 | — | — | — | — | — | 4.5 | 4.5 | 4 | 4 | 0 | 0 |
| 5 | 2 | x | — | — | — | ± | 5 | 5 | 5 | 5 | 5 | 4 |
| | 0.5 | ± | — | — | — | — | 5 | 5 | 5 | 5 | 4 | 1 |
| | 0.25 | — | — | — | — | — | 5 | 5 | 5 | 5 | 1 | 0 |
| | 0.12 | — | — | — | — | — | 3.5 | 4.5 | 5 | 4 | 0 | 0 |
| | 0.06 | — | — | — | — | — | 3 | 3 | 3 | 3 | 0 | 0 |
| 6 | 2 | x | — | + | — | — | 5 | 5 | 5 | 5 | 5 | 5 |
| | 0.5 | ± | — | — | — | — | 5 | 5 | 5 | 5 | 1 | 3 |
| | 0.25 | — | — | — | — | — | 5 | 5 | 5 | 5 | 0 | 0 |
| | 0.12 | — | — | — | — | — | 4 | 4.5 | 3 | 2 | 0 | 0 |
| | 0.06 | — | — | — | — | — | 1 | 1 | 0 | 1 | 0 | 0 |
| 7 | 2 | ++ | — | — | ++ | — | 5 | 5 | 5 | 5 | 5 | 5 |
| | 0.5 | — | — | — | — | — | 5 | 5 | 5 | 5 | 4 | 4 |
| | 0.25 | — | — | — | — | — | 5 | 5 | 5 | 5 | 2 | 2 |
| | 0.12 | — | — | — | — | — | 3 | 3 | 4 | 2 | 0 | 2 |
| | 0.06 | — | — | — | — | — | 2 | 2 | 4 | 0 | 0 | 0 |
| 8 | 2 | ++ | — | — | ++ | — | 5 | 5 | 5 | 5 | 5 | 5 |
| | 0.5 | — | — | — | — | — | 5 | 5 | 5 | 5 | 5 | 5 |
| | 0.25 | — | — | — | — | — | 5 | 5 | 5 | 5 | 5 | 3 |

TABLE III-continued

| Compound No. | Dose (a.i.kg/ha) | Crop Injury | | | | | Herbicidal Effect | | | | | |
|---|---|---|---|---|---|---|---|---|---|---|---|---|
| | | A | B | C | D | E | F | G | H | I | J | K |
| | 0.12 | — | — | — | — | — | 4 | 4 | 4 | 1 | 1 | 0 |
| | 0.06 | — | — | — | — | — | 2 | 0 | 2 | 0 | 0 | 0 |
| 9 | 2 | +++ | — | — | ++ | ++ | 5 | 5 | 5 | 5 | 5 | 5 |
| | 0.5 | — | — | — | — | — | 5 | 5 | 5 | 5 | 4 | 3 |
| | 0.25 | — | — | — | — | — | 4 | 5 | 4 | 5 | 1 | 1 |
| | 0.12 | — | — | — | — | — | 4 | 5 | 4 | 5 | 0 | 0 |
| | 0.06 | — | — | — | — | — | 1 | 2 | 1 | 1 | 0 | 0 |
| 10 | 2 | ± | — | — | x | + | 5 | 5 | 5 | 5 | 5 | 5 |
| | 0.5 | — | — | — | ± | — | 5 | 5 | 5 | 5 | 5 | 5 |
| | 0.25 | — | — | — | — | — | 5 | 5 | 5 | 5 | 5 | 5 |
| | 0.12 | — | — | — | — | — | 5 | 4 | 3 | 4.5 | 2 | 3 |
| | 0.06 | — | — | — | — | — | 2 | 0 | 0 | 1 | 1 | 0 |
| 11 | 2 | x | — | — | ++ | — | 5 | 5 | 5 | 5 | 5 | 5 |
| | 0.5 | ± | — | — | ± | — | 5 | 5 | 5 | 5 | 5 | 5 |
| | 0.25 | — | — | — | — | — | 5 | 5 | 5 | 5 | 5 | 1 |
| | 0.12 | — | — | — | — | — | 5 | 4.5 | 4 | 4 | 4 | 0 |
| | 0.06 | — | — | — | — | — | 2 | 0 | 3 | 2 | 1 | 0 |
| 12 | 2 | x | — | — | ± | — | 5 | 5 | 5 | 5 | 5 | 5 |
| | 0.5 | ± | — | — | — | — | 5 | 5 | 5 | 5 | 2 | 1 |
| | 0.25 | — | — | — | — | — | 5 | 5 | 5 | 5 | 0 | 0 |
| | 0.12 | — | — | — | — | — | 5 | 5 | 5 | 5 | 0 | 0 |
| | 0.06 | — | — | — | — | — | 4 | 3 | 4 | 2 | 0 | 0 |
| 13 | 2 | + | — | — | ++ | + | 5 | 5 | 5 | 5 | 5 | 5 |
| | 0.5 | — | — | — | — | — | 5 | 5 | 5 | 5 | 3 | 3 |
| | 0.25 | — | — | — | — | — | 4 | 5 | 5 | 4.5 | 2 | 1 |
| | 0.12 | — | — | — | — | — | 2 | 4.5 | 1 | 3 | 0 | 1 |
| | 0.06 | — | — | — | — | — | 0 | 2 | 0 | 0 | 0 | 0 |
| 14 | 2 | x | — | — | — | ++ | 5 | 5 | 5 | 5 | 5 | 5 |
| | 0.5 | + | — | — | — | — | 5 | 5 | 5 | 5 | 5 | 1 |
| | 0.25 | — | — | — | — | — | 5 | 5 | 5 | 2 | 3 | 0 |
| | 0.12 | — | — | — | — | — | 1 | 4 | 2 | 0 | 0 | 0 |
| | 0.06 | — | — | — | — | — | 0 | 2 | 0 | 0 | 0 | 0 |
| 15 | 2 | +++ | — | — | + | + | 5 | 5 | 5 | 5 | 3 | 3 |
| | 0.5 | — | — | — | — | — | 5 | 5 | 5 | 5 | 1 | 1 |
| | 0.25 | — | — | — | — | — | 3.5 | 5 | 1 | 0 | 0 | 0 |
| | 0.12 | — | — | — | — | — | 1 | 2 | 0 | 0 | 0 | 0 |
| | 0.06 | — | — | — | — | — | 0 | 0 | 0 | 0 | 0 | 0 |
| 16 | 2 | — | — | ± | ++ | ++ | 5 | 5 | 5 | 5 | 5 | 5 |
| | 0.5 | — | — | — | — | — | 5 | 5 | 5 | 5 | 5 | 5 |
| | 0.25 | — | — | — | — | — | 5 | 5 | 5 | 5 | 5 | 5 |
| | 0.12 | — | — | — | — | — | 5 | 5 | 5 | 5 | 4 | 5 |
| | 0.06 | — | — | — | — | — | 5 | 5 | 5 | 5 | 3 | 2 |
| 18 | 2 | ± | — | ± | ± | — | 5 | 5 | 5 | 5 | 5 | 5 |
| | 0.5 | — | — | — | — | — | 5 | 5 | 5 | 5 | 5 | 1 |
| | 0.25 | — | — | — | — | — | 4.5 | 4.5 | 4 | 4 | 4.5 | 0 |
| | 0.12 | — | — | — | — | — | 1 | 4 | 4 | 4 | 2 | 0 |
| | 0.06 | — | — | — | — | — | 1 | 2 | 2 | 2 | 2 | 0 |
| 19 | 2 | + | — | + | + | ± | 5 | 5 | 5 | 5 | 5 | 4 |
| | 0.5 | ± | — | ± | ± | — | 5 | 5 | 5 | 5 | 4 | 3 |
| | 0.25 | — | — | — | — | — | 4.5 | 5 | 5 | 4.5 | 2 | 0 |
| | 0.12 | — | — | — | — | — | 3.5 | 4.5 | 4.5 | 4.5 | 1 | 0 |
| | 0.06 | — | — | — | — | — | 2 | 3.5 | 3.5 | 3.5 | 1 | 0 |
| 20 | 2 | + | ± | ± | + | + | 5 | 5 | 5 | 5 | 5 | 5 |
| | 0.5 | ± | — | — | ± | ± | 5 | 5 | 5 | 5 | 4.5 | 4 |
| | 0.25 | — | — | — | — | — | 5 | 5 | 5 | 5 | 2 | 2 |
| | 0.12 | — | — | — | — | — | 5 | 5 | 5 | 5 | 1 | 1 |
| | 0.06 | — | — | — | — | — | 4 | 4.5 | 4.5 | 4 | 1 | 1 |
| 21 | 2 | ± | — | ± | + | + | 5 | 5 | 5 | 5 | 4 | 4 |
| | 0.5 | — | — | — | ± | ± | 5 | 5 | 5 | 5 | 2 | 3 |
| | 0.25 | — | — | — | — | — | 4 | 4.5 | 4 | 4.5 | 0 | 0 |
| | 0.12 | — | — | — | — | — | 3.5 | 4.5 | 4 | 4 | 0 | 0 |
| | 0.06 | — | — | — | — | — | 2 | 4 | 3.5 | 3 | 0 | 0 |
| Comparative Agent b | 2 | ± | — | + | x | x | 5 | 5 | 5 | 5 | 5 | 5 |
| | 0.5 | — | — | — | + | — | 5 | 5 | 5 | 5 | 5 | 5 |
| | 0.25 | — | — | — | — | — | 5 | 5 | 5 | 5 | 4.5 | 2 |
| | 0.12 | — | — | — | — | — | 5 | 5 | 5 | 5 | 2 | 2 |
| | 0.06 | — | — | — | — | — | 4.5 | 4 | 3 | 3 | 0 | 0 |
| Comparative Agent c | 2 | x | + | ++ | x | x | 5 | 5 | 5 | 5 | 5 | 5 |
| | 0.5 | +++ | ± | ± | x | ± | 5 | 5 | 5 | 5 | 5 | 5 |
| | 0.25 | ++ | — | — | + | — | 5 | 5 | 5 | 5 | 5 | 5 |
| | 0.12 | ± | — | — | — | — | 5 | 5 | 5 | 5 | 4 | 3 |
| | 0.06 | — | — | — | — | — | 5 | 5 | 5 | 5 | 3 | 3 |
| Comparative Agent d | 2 | x | ++ | ++ | x | x | 5 | 5 | 5 | 5 | 5 | 5 |
| | 0.5 | +++ | + | + | ++ | ± | 5 | 5 | 5 | 5 | 5 | 5 |
| | 0.25 | ++ | ± | — | ± | — | 5 | 5 | 5 | 5 | 5 | 2 |
| | 0.12 | ± | — | — | — | ± | 5 | 5 | 5 | 5 | 3 | 1 |

TABLE III-continued

| Compound No. | Dose (a.i.kg/ha) | Crop Injury | | | | | Herbicidal Effect | | | | |
|---|---|---|---|---|---|---|---|---|---|---|---|
| | | A | B | C | D | E | F | G | H | I | J | K |
| | 0.06 | — | — | — | — | — | 4.5 | 4.5 | 4.5 | 5 | 1 | 0 |

Notes:
b: 2-chloro-2',6'-diethyl-N—methoxymethyl acetanilide;
c: 2-chloro-2',6'-dimethyl-N—pyrazolylmethyl acetanilide;
d: 2-chloro-2'-methyl-6'-methoxy-N—pyrazolylmethyl acetanilide;
A: corn (*Zea mays*);
B: soybean (*Glycine max*);
C: cotton (*Gossypium hirsutum*);
D: sugar beet (*Beta vulgaris*);
E: sunflower (*Helianthus annuus*);
F: barnyardgrass (*Echinochloa crusgalli*);
G: crabgrass (*Digitaria adscendens*);
H: green foxtail (*Setaria viridis*);
I: *Paspalum thumbergii*;
J: redroot pigweed (*Amaranthus retroflexus*);
K: pale smartweed (*Polygonum lapathifolium*)

The preparation methods of the herbicide in accordance with the present invention are hereunder described. It should however be understood that the scope of the present invention is by no means limited to the following description. All parts are by weight unless otherwise indicated.

Preparation 1: Granule

A premix of Compound No. 1 (5 parts), bentonite (50 parts), talc (40 parts), sodium dodecylbenzenesulfonate (2 parts), sodium ligninsulfonate (2 parts) and polyoxyethylene alkyl allyl ether (1 part) was blended with a suitable amount of water. The mixture was processed in a granulator to provide 100 parts of a granule. Granules of Compound Nos. 2 to 21 were also prepared by the same method.

Preparation 2: Wettable powder

A mix of Compound No. 1 (20 parts), diatomaceous earth (60 parts), white carbon (15 parts), sodium ligninsulfonate (3 parts) and sodium dodecylbenzenesulfonate (2 parts) was ground into tiny particles in a kneader to make 100 parts of a wettable powder. Wettable powders of Compound Nos. 2 to 21 were also prepared by the same method.

Preparation 3: Emulsifiable concentrate

Thirty parts of Compound No. 1 was dissolved in a liquid mixture of xylene (55 parts), cyclohexanone (10 parts), calcium dodecylbenzenesulfonate (3 parts) and polyoxyethylene alkyl allyl ether (2 parts) to make 100 parts of an emulsifiable concentrate. Emulsifiable concentrates of Compound Nos. 2 to 21 were also prepared by the same method.

While the invention has been described in detail and with reference to specific embodiments thereof, it will be apparent to one skilled in the art that various changes and modifications can be made therein without departing from the spirit and scope thereof.

What is claimed is:

1. An acetanilide derivative of formula (I):

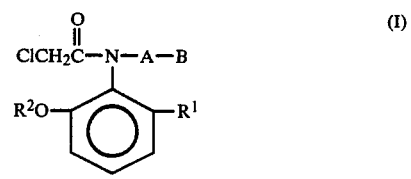

wherein $R^1$ is a lower alkyl group; $R^2$ is a fluorine-substituted lower alkyl group; A is

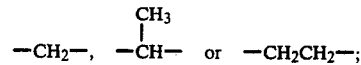

or —CH$_2$CH$_2$—; B is hydrogen, lower alkoxy, pyrazolyl or pyrazolyl substituted by lower alkyl.

2. A herbicidal composition, comprising:
as the active ingredient, a herbicidally effective amount of at least one acetanilide derivative of formula (I):

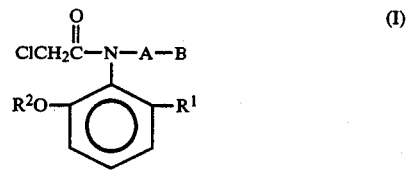

wherein $R^1$ is a lower alkyl group; $R^2$ is a fluorine-substituted lower alkyl group; A is

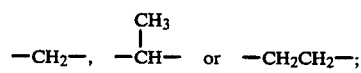

B is hydrogen, lower alkoxy, pyrazolyl or pyrazolyl substituted by lower alkyl.

3. The herbicidal composition as claimed in claim 2, wherein said herbicidal composition is dispersed in water or is formulated in the form of an emulsifiable concentrate, a liquid formulation, a wettable powder, a dust or as granules.

4. The herbicidal composition as claimed in claim 2, wherein said herbicidal composition is applied in an amount of 0.015 to 10 kg per hectare.

5. The herbicidal composition as claimed in claim 4, wherein said herbicidal composition is applied in an amount of 0.25 to 5 kg per hectare.

* * * * *